United States Patent [19]

Smith et al.

[11] 3,965,156

[45] *June 22, 1976

[54] PROCESS FOR PREPARING VINYL ESTERS OF CARBOXYLIC ACIDS

[75] Inventors: William E. Smith, Schenectady; R. John Gerhart, Averill Park, both of N.Y.

[73] Assignee: General Electric Company, Pittsfield, Mass.

[ * ] Notice: The portion of the term of this patent subsequent to June 22, 1993, has been disclaimed.

[22] Filed: Feb. 4, 1974

[21] Appl. No.: 439,444

[52] U.S. Cl. .................... 260/491; 260/410.9 N; 260/604 AC
[51] Int. Cl.$^2$ .......................................... C07C 67/00
[58] Field of Search ............... 260/497 A, 410.9 N, 260/491

[56] References Cited
UNITED STATES PATENTS 3,444,189   5/1969   Olivier ........................... 260/497 A

FOREIGN PATENTS OR APPLICATIONS 1,443,882   10/1968   Germany ....................... 260/497 A

OTHER PUBLICATIONS

Saminos, *Jour. of Catalysis* 23, 19–30 (1971).

*Primary Examiner*—Lorraine A. Weinberger
*Assistant Examiner*—Michael Shippen
*Attorney, Agent, or Firm*—Donald M. Papuga; William F. Mufatti

[57] ABSTRACT

A process for preparing vinyl esters of carboxylic acids which comprises reacting a mixture of a lower alkyl carboxylate ester, water, and the corresonding carboxylic acid and alcohol with ethylene and oxygen in the presence of an oxidation catalyst.

4 Claims, No Drawings

PROCESS FOR PREPARING VINYL ESTERS OF CARBOXYLIC ACIDS

This invention relates to a process for preparing vinyl esters of carboxylic acids which comprises reacting a mixture of a lower alkyl carboxylate ester, water, and the corresponding carboxylic acid and alcohol with ethylene and oxygen in the presence of a catalyst comprising a Group VIII noble metal, or its salts, or its oxides, or mixtures thereof.

BACKGROUND OF THE INVENTION

Vinyl esters of carboxylic acids have been prepared by a number of different methods. A useful method of preparing vinyl acetate, for example, is by contacting ethylene with a palladium catalyst in the presence of oxygen and acetic acid. This is illustrated by U.S. Pat. No. 3,658,888, for example. Vinyl acetate is useful as an intermediate for the manufacture of polymers and other valuable materials.

DESCRIPTION OF THE INVENTION

The primary object of the present invention concerns a process for preparing vinyl esters of carboxylic acids which comprises reacting a mixture of a lower alkyl carboxylate ester, water and the corresponding carboxylic acid and alcohol with ethylene and oxygen in the presence of a catalyst comprising a Group VIII noble metal, or its salts, or its oxides, or mixtures thereof. Preferably, the lower alkyl carboxylate ester is methyl acetate.

As described, supra, a useful method of preparing vinyl esters of carboxylic acids is by reaction of ethylene and the appropriate carboxylic acid under oxidation conditions as illustrated, for the case of vinyl acetate, in Equation 1.

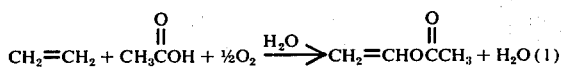

If the vinyl ester so produced is to be used in a subsequent process that involves liberation of the carboxylate moiety as part of another ester, then said ester can be hydrolyzed (equation 2) by methods known in the art to make available the carboxylic acid for recycle to the original oxidation.

As indicated in equation 2, however, the hydrolysis is an equilibrium process; isolation of the carboxylic acid requires repeated equilibrations and distillations and is thus inconvenient.

It has been discovered that the recycle can be performed with much greater efficiency by subjecting the alkyl carboxylate to hydrolysis and using the hydrolysis mixture itself (containing the carboxylic acid, alcohol, water and unconverted ester, preferably at equilibrium) directly in the oxidation step. The alcohol and ester present cause essentially no deleterious effects in the operation; they pass through unchanged and suitable for use in recycle or in a subsequent step. Optionally, an acidic co-catalyst may be employed. In such cases, the hydrolysis represented in equation 2 can be made to proceed significantly further toward completion.

The lower alkyl carboxylate esters which may be employed in the instant invention are illustrated by the following structure:

wherein $R_1$ and $R_2$ can contain from one to about eight carbon atoms. The preferred lower alkyl carboxylate ester is methyl acetate.

The oxidation catalyst comprises a Group VIII noble metal, or its salts, or its oxides, or mixtures thereof. Specific examples of such catalysts include metals such as palladium, ruthenium, rhodium, platinum, osmium, and iridium as well as oxides and salts such as palladous propionate, palladous benzoate, palladous chloride, palladous bromide, palladous oxide, etc., ruthenium acetate, etc., rhodium acetate, etc., platinous benzoate, platinum dichloride, platinum oxide, etc., iridium chloride, etc., and the like and mixtures thereof.

The preferred catalyst is a mixture of the Group VIII noble metal and its salt. A more preferred catalyst is a mixture of palladium and palladous acetate.

A promoter may be added to the catalyst which influences activity and selectivity. Among the preferred promoters are the alkali metal and alkaline earth metal carboxylates, the transition metals, their salts, gold or copper.

The optional acidic co-catalyst may be an acidic support material such as alumina or silica or the like or may be a more active substance present in smaller amounts.

The catalyst may be prepared in a number of different ways. For example, a support such as carbon or alumina is impregnated with a palladium acetyl acetonate solution in benzene and dried. The resulting material is then impregnated with a solution of potassium acetate in water and dried. The catalyst is then treated with ethylene, which reduces the palladium to the metallic state. The catalyst thus obtained contains palladium metal and potassium acetate is about 1:10 parts.

Varying amounts of the catalyst can be used within the scope of this invention. Amounts as low as about 0.1% based on weight of support have been found to be effective.

The working temperature is in the range of from about 100° to about 200°C. For optimum production of the vinyl carboxylate, the temperature is in the range from about 125° to about 160°C. The working pressure is in the range from about atmospheric to about 150 psi. Somewhat higher or lower temperatures and pressures may, however, be used within the scope of the invention.

The oxygen in the instant process may be used in pure elementary form or in admixture with inert gases, for example, in the form of air. However, it is preferred to work with concentrated oxygen.

The ethylene in the instant process may be used in pure form or in admixture with inert compounds, for example, saturated hydrocarbons.

The invention is illustrated for the case of vinyl acetate. A mixture of methyl acetate, water, acetic acid and methanol is passed through a bed of the catalyst in a tube reactor with ethylene and oxygen at temperatures of from about 100° to about 160°C. at about 80 psi. Upon leaving the reaction zone, the products are condensed and a two phase mixture forms. The upper phase is a mixture of, in this case, methyl acetate, vinyl acetate and methanol. The lower phase is principally water and methanol, with a small amount of vinyl acetate. Direct distillation of the mixture affords the methanol and methyl acetate for recycle, leaving a two phase mixture of vinyl acetate and water. The vinyl acetate phase is decanted in a form suitable for further use.

The alkyl carboxylate ester hydrolysis mixture (derived from methyl acetate, for example) may be supplemented with more of the carboxylic acid (for example, acetic acid) with equally satisfactory results.

As is known in the art (Encyclopedia of Polymer Science and Technology, Vol. 15 *Vinyl Acetate Polymers*, pp. 577–677, Interscience, New York, 1971) vinyl acetate may be converted directly to poly(vinyl acetate). As is also known in the art (Encyclopedia of Polymer Science and Technology, Vol. 14, *Vinyl Alcohol Polymers*, pp. 149–239. Interscience, New York, 1971), the poly(vinyl acetate) on reaction with methanol is converted to poly(vinyl alcohol), with liberation of the acetate moiety as methyl acetate. The above references to the Encyclopedia of Polymer Science and Technology are incorporated herein by reference. Thus, with recycle of the methyl acetate, an efficient and economical overall process for producing poly(vinyl alcohol) from ethylene is possible (equations 4-6).

of 740 grams of methyl acetate and 170 grams of methanol) and 900 grams of water is passed through under 80 psi pressure. The effluent contains, according to quantitative glpc analysis, 282 grams of acetic acid, 320 grams of methanol, 393 grams of methyl acetate, and 815 grams of water. (The composition is essentially the same after a second pass, demonstrating that equilibrium has been reached.) These results indicate that for equation 7, K = 0.2 under these conditions.

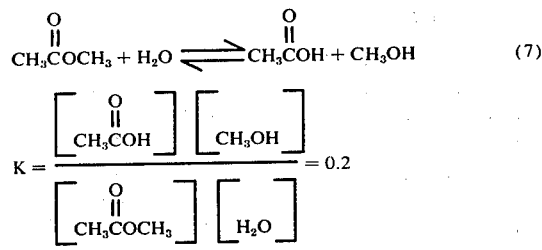

The hydrolysate is cooled to about 150°C. and mixed with (per hour) 1500 grams of ethylene and 170 grams of oxygen. The resultant mixture is passed directly through a second 8 ft. × 1 inch diameter tube containing 1 liter of catalyst composed of 4–8 mesh carbon impregnated with palladium (0.3%) and potassium acetate (3%), and operated at 160°C. at 80 psi pressure. The output per hour from this oxidation zone is a mixture (two liquid phases on cooling) composed of, according to quantitative glpc analysis, 379 grams of unconverted methyl acetate (57% recovery), 388 grams of vinyl acetate (92% yield based on 49% con-

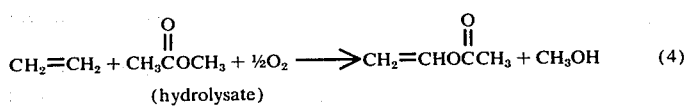

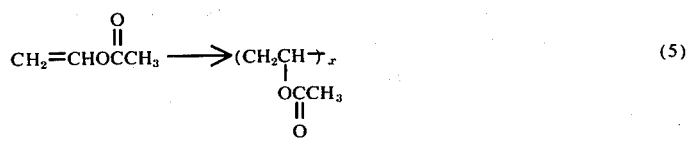

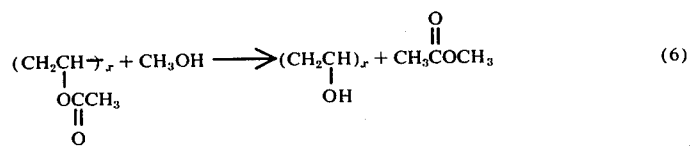

DESCRIPTION OF THE PREFERRED EMBODIMENT

The following Examples are set forth to illustrate more clearly the principal and practice of this invention to those skilled in the art. Unless otherwise specified, where parts or percents are mentioned, they are parts or percents by weight.

EXAMPLE 1

An 8 ft. × 1 inch diameter stainless steel tube is charged with one liter (1000 grams) of alumina catalyst (1/8 inch pellets, Harshaw Al-1802-E 1/8) and maintained at 250°C. while a mixture per hour of 910 grams of the methyl acetate-methanol azeotrope (composed version), 318 grams of methanol, traces of acetaldehyde and acetic acid, and the excess water and ethylene.

EXAMPLE 2

The tandem tube reactors are operated as described in Example 1, with the amount of water used per hour doubled to 1800 grams. Analysis of the condensed phases indicates the collection per hour of 249 grams of methyl acetate (34% unconverted), 505 grams of vinyl acetate (89% yield based on 66% conversion), and 368 grams of methanol.

EXAMPLE 3

The tandem tube reactors are operated as in Example 1, with substitution of 740 grams per hour of pure methyl acetate for the methyl acetatemethanol azeotrope. Analysis of the condensed phases indicates the collection per hour of 298 grams of methyl acetate (40% unconverted), 469 grams of vinyl acetate (91% yield based on 60% conversion), and 179 grams of methanol (93% yield).

EXAMPLE 4

The tandem tube reactors are operated as described in Example 2, with substitution of 740 grams per hour of pure methyl acetate for the methyl acetate-methanol azeotrope. Analysis of the condensed phases indicates the collection per hour of 209 grams of methyl acetate (28% unconverted), 543 grams of vinyl acetate (88% yield based on 72% conversion), and 193 grams of methanol (84% yield).

EXAMPLE 5

The procedure described in Example 1 is followed, but with the palladium oxidation catalyst and potassium acetate mounted on alumina of the type used in the hydrolysis zone. The effluent produced in this case contains 339 grams of methyl acetate (46% unconverted), 381 grams of vinyl acetate, 84 grams of acetaldehyde, and 298 grams of methanol.

EXAMPLE 6

A 6 inch × ¼ inch diameter stainless steel tube packed with an acidic ion exchange resin (Dowex 50 W × 8) is heated at 140°C. while a mixture per hour of 546 grams of the methyl acetate-methanol azeotrope (composed of 444 grams of methyl acetate and 102 grams of methanol) and 540 grams of water is passed through under 140 psi pressure. The mixture produced is the equilibrium hydrolysate (k = 0.2), suitable for use in the oxidation stage as described in Example 1.

EXAMPLE 7

A mixture of 740 grams of methyl acetate, 170 grams of methanol and 900 grams of water is combined with 25 grams of acidified aluminum silicate powder (Filtrol 20) and heated at 67°–72°C. for 1 hour. The catalyst is filtered off, leaving an equilibrium hydrolysate (K = 0.15) suitable for use in the oxidation stage as described in Example 1.

Obviously, other modifications and variations of the present invention are possible in the light of the above teachings. It is therefore to be understood that changes may be made in the particular embodiments of the invention described which are within the full intended scope of the invention as defined by the appended claims.

What is claimed is:

1. A vapor phase process for preparing vinyl esters of carboxylic acids which comprises reacting a mixture of a lower alkyl carboxylate ester, water, and the corresponding carboxylic acid and alcohol with ethylene and oxygen in the presence of a catalyst consisting of Group VIII noble metal, or its salts, or its oxides, or mixtures thereof and optionally an acidic support material and optionally a promoter selected from the group consisting of alkali metal carboxylates, alkaline earth carboxylates, the transition metals, their salts, gold or copper at a temperature of from about 100°C to about 200°C.

2. The process of claim 1 wherein the catalyst comprises a mixture of palladium and palladous acetate.

3. The process of claim 1 wherein the mixture of the lower alkyl carboxylate, water and the corresponding carboxylic acid and alcohol is at equilibrium.

4. A vapor phase process of preparing vinyl acetate which comprises reacting ethylene, a mixture of methyl acetate, water, acetic acid, and methanol and oxygen in the presence of a catalyst consisting of a Group VIII noble metal, or its salts, or its oxides, or mixtures thereof and optionally an acidic support material and optionally a promoter selected from the group consisting of alkali metal carboxylates, alkaline earth carboxylates, the transition metals, their salts, gold or copper at a temperature of from about 100° to 160°C.

* * * * *